(12) United States Patent
Carrieri

(10) Patent No.: US 6,389,408 B1
(45) Date of Patent: May 14, 2002

(54) NEURAL NETWORK SYSTEMS FOR CHEMICAL AND BIOLOGICAL PATTERN RECOGNITION VIA THE MUELLER MATRIX

(75) Inventor: Arthur H. Carrieri, Abingdon, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/343,621

(22) Filed: Jun. 30, 1999

(51) Int. Cl.[7] .............................................. G06F 9/445
(52) U.S. Cl. ......................... 706/48; 382/156; 382/157
(58) Field of Search ................................. 382/159, 154, 382/100, 157, 169; 706/41, 48, 20; 356/367, 343, 456; 702/28

(56) References Cited

U.S. PATENT DOCUMENTS 5,631,469 A    5/1997    Carrieri et al. .......... 250/341.5

*Primary Examiner*—Thomas Black
*Assistant Examiner*—Michael B. Holmes
(74) *Attorney, Agent, or Firm*—Ulysses John Biffoni; Vincent J. Ranucci

(57) ABSTRACT

A neural network pattern recognition system for remotely sensing and identifying chemical and biological materials having a software component having an adaptive gradient descent training algorithm capable of performing backward-error-propagation and an input layer that is formatted to accept differential absorption Mueller matrix spectroscopic data, a filtering weight matrix component capable of filtering pattern recognition from Mueller data for specific predetermined materials and a processing component capable of receiving the pattern recognition from the filtering weight matrix component and determining the presence of specific predetermined materials. A method for sensing and identifying chemical and biological materials also is disclosed.

12 Claims, 2 Drawing Sheets

Figure 1:
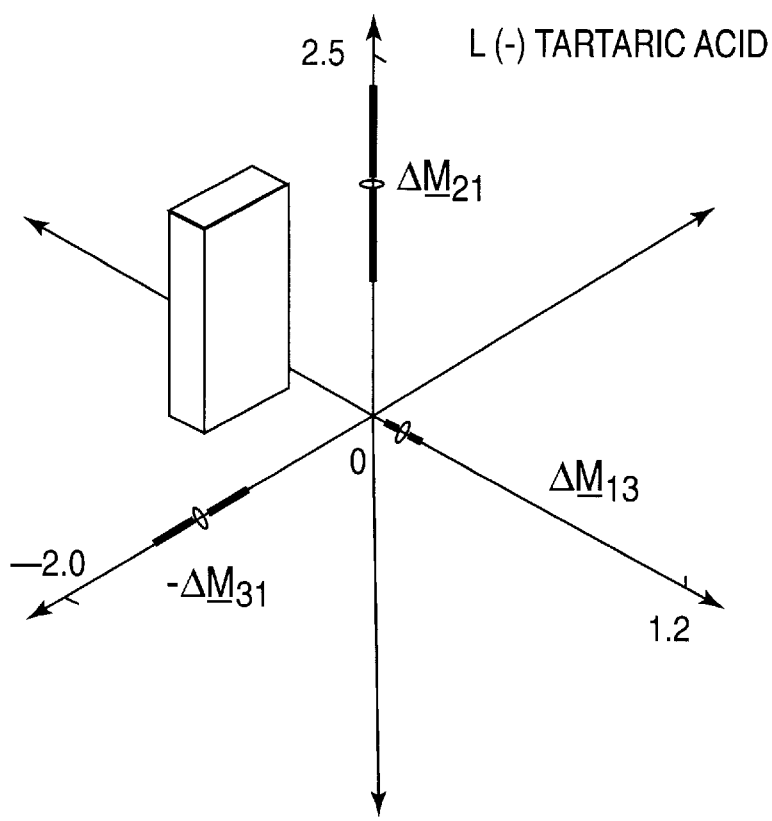
Figure 1:
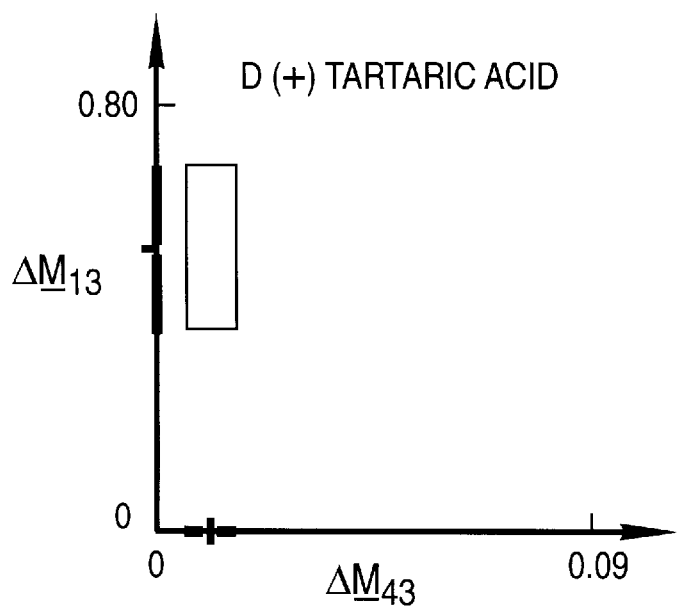

NEURAL NETWORK SYSTEMS FOR CHEMICAL AND BIOLOGICAL PATTERN RECOGNITION VIA THE MUELLER MATRIX

GOVERNMENT INTEREST

The invention described herein may be manufactured, licensed, and used by or for the U.S. Government.

BACKGROUND OF THE INVENTION

1. Field of the Invention

The present invention relates to a neural network pattern recognition system that identifies chemical and/or biological materials (CBMs) at a distance by recognizing the material's light scattering signature. More particularly, the present invention trains a neural network system to perform pattern recognition from susceptible Mueller matrix elements derived from modulated polarized infrared laser light that is scattered from a contaminated surface on and off an absorption band of the CBM target (contaminant). The neural network acts as a filter that identifies any-of-N compounds in real-time through their unique differential-absorption Mueller matrix properties.

2. Brief Description of the Related Art

Infrared (IR) luminescence, polarized scattering, and volume reflectance technologies have been evaluated as stand-off detection methods for chemical and biological warfare agents (CBWA) deposited on terrain and man-made landscapes. Back-reflectance techniques have involved spectroscopic measurements of a depolarized, multiple-scattered subsurface IR radiance component from soil and sand wetted by several simulants of liquid chemical warfare agents. Generally these methods have proven insensitive as they tend to detect a simulant's absorption bands far above a threshold volume concentration considered life threatening had the contaminant been nerve agent, such as VX. However, the active multiwavelength polarized backscattering and "pseudo-active" thermal luminescence methods of remote detection have shown improved sensitivity and accuracy. One active technique called differential absorption Mueller matrix spectroscopy, or DIAMMS, has shown promise for solving the combined CBWA detection problem.

Neural network analysis of polarized light scattering can be applied to identify biological and chemical contaminants by a system in which monochromatic polarization-modulated infrared laser light is backscattered by the contaminants at two close wavelengths. One beam wavelength corresponds to an absorption band of the scatterer while the other wavelength is nonabsorbing. The light beams backscattered by the contaminant are examined in the form of a Mueller matrix whose elements describe all polarization states of the backscattered light at each pixel of the detector array. Mueller matrices are mathematical calculations and representations of irradiated materials. They consist of 16 elements, and completely describe both the geometric (particle size) and physical (refractive index) aspects of the scatterer. These neural network systems filter the unique pattern of susceptible Mueller matrix elements of 15 or less normalized difference-elements of the CBMs. Characteristics such as particle size, particle shape, refractive index, and the like, can be correlated.

U.S. Pat. No. 4,306,809 (Azzam), U.S. Pat. No. 4,953,980 (DeVolk et al.), U.S. Pat. No. 4,884,886 (Salzman et al.), U.S. Pat. No. 5,247,176 (Goldstein), U.S. Pat. No. 5,631,469 (Carrieri et al.), U.S. Pat. No. 5,659,391 (Carrieri), and U.S. Pat. No. 5,708,503 (Carrieri) disclose many aspects of passive and active systems which process and transform scattergrams into Mueller elements, the disclosures of these patents are incorporated herein by reference.

SUMMARY OF THE INVENTION

In view of the foregoing, it is an object of the present invention to provide neural network training sufficient for CBWA detection.

It is further an object of the present invention to provide training of neural networks for selective CBM identification and improved efficiency of using Mueller matrix elements in CBM identification.

These and other objects are accomplished with the present invention that includes a neural network pattern recognition system for remotely sensing and identifying chemical and biological materials comprising a software component having an adaptive gradient descent training algorithm capable of performing backward-error-propagation and an input layer is formatted to accept differential absorption Mueller matrix spectroscopic data, a filtering weight matrix component capable of filtering pattern recognition from Mueller data for specific predetermined materials, and, a processing component capable of receiving the pattern recognition from the filtering weight matrix component and determining the presence of specific predetermined materials.

The present invention further includes a method for sensing and identifying chemical and biological materials comprising a software component having an adaptive gradient descent training algorithm capable of performing backward-error-propagation and an input layer is formatted to accept differential absorption Mueller matrix spectroscopic data, a filtering weight matrix component capable of filtering pattern recognition from Mueller data for specific predetermined materials, and, a processing component capable of receiving the pattern recognition from the filtering weight matrix component and determining the presence of specific predetermined materials, building artificial neural network systems for detecting specific solid organic compounds by pattern recognition of their polarized light scattering signatures, and discerning the presence of specific analytes within a sample based upon cued susceptive Mueller matrix difference elements.

BRIEF DESCRIPTION OF DRAWINGS

FIG. 1 is a representation of the scaled and distributed difference Mueller matrix elements most susceptive to stereoisomers of tartaric acid in backscattering on and off its molecular vibrational resonance line plotted in Mueller matrix space, showing the three most significant difference elements of levorotary tartaric acid and the two most significant difference elements of dextrorotary tartaric acid; and, FIG. 2 is a flowchart of the DIAMMS data processing hardware unit.

DETAILED DESCRIPTION OF THE PREFERRED EMBODIMENTS

The present invention is a neural network pattern recognition system that trains a processor to recognize chemical and biological polarized light back-scattering information from an infrared excitation. Neural network pattern recognition via DIAMMS involves the digital acquisition of raw scattergrams in the form of the sensor's output voltage waveform, the electronic transformation of the scattergrams into elements of the Mueller matrix, the Mueller matrix element subtraction and auto-scaling, and mathematical filtration operations that select and process susceptible normalized elements from a field of 15, i.e., the feature detection domains. Feed-forwarding of these discriminating matrix difference elements, along with statistics and header data, through the input layer of a trained neural network system produces real numbers at the network output layer nodes. The numerical range of nodal outputs is usually bounded by the network transfer function, or synapse, fully connecting nodes between layers and responsible for internodal signal conduction, in the form of firing of neurons. By performing normalized inner products of this output vector with the network training set of output vectors, and by comparing the result to a selected threshold limit, such as 0.98 to 1.00, a deciding line for a detection event is created. The entire decision making process, from digital data acquisition to pattern recognition, may be accomplished in sub-second time frames.

An apparatus for remotely sensing and identifying CBMs having an interrogation component, a collection component, an optical analysis component, a filter component, and a comparison component is disclosed in U.S. patent application Ser. No. 09/226,631, entitled "Infrared Mueller Matrix Detection and Ranging System", by Arthur H. Carrieri, filed on Dec. 21, 1998, the disclosure of which is herein incorporated by reference and now U.S. Pat. No. 6,060,710. The disclosed apparatus uses an active remote sensing system, or stand-off surface contamination detection sensor comprising a photopolarimeter, that identifies possible CBMs at a distance by interrogating suspect materials with infrared laser light from the interrogation component. The radiation produces backscattering from the CBMs, which are used to distinguish particular CBMs on a surface. Specific backscattered laser radiation information is collected from the CBMs by the collection component, which is electronically recorded and mathematically analyzed through the optical analysis component. The information is transformed using the transform component which produces a Mueller matrix. Selective Mueller matrix elements are compared with known data using the comparison component to identify known CBMs.

In the present invention, the known data comprises artificial neural network systems built for detecting amino acids, sugars, and other solid organic compounds by pattern recognition of their polarized light scattering signatures. The present invention provides network training using backward-error propagation and adaptive gradient descent methods. The training produces a weight matrix that, when applied as a filter, discerns the presence of the compound analytes based upon cued susceptive Mueller matrix difference elements. The present invention may be implemented as a software or hardware module to a differential absorption Mueller matrix spectrometer.

Neural Network Modeling Data Format

Multiwavelength Mueller matrices measured via DIAMMS comprise a group of differential-elements that uniquely represent simulants of CBWA material in backscattering from pulsating and polarization (phase) modulating pairs of infrared laser beams. These differential elements are selected from magnitudes in beam backscattering measurements on and off an IR absorption band of the simulant or analyte. They are generally a minor subset of the full 16-element Mueller matrix field, per pair of irradiating $CO_2$ laser beams.

Differential-element features that uniquely represent each of sixteen crystalline biosimulant test compounds were measured. These compounds included DL-alanine (racemic amino acid; $CH_3CH(NH_2)COOH$), L-alanine (amino acid; $CH_3CH(NH_2)COOH$), DL-aspartic (amino) acid ($HOOCH_2CH(NH_2)COOH$), (1R)-(+)-camphor(1,7,7-Trimethyl-2.2.1]heptan-2-one), (1S)-(−)-camphor ($C_{10}H_{12}O$), D-fructose (fruit sugar, $C_6H_{12}O_6$), D-glucose (blood sugar, $C_6H_{12}O_6$), L-histidine (amino acid, glyoxaline-5-alanine), D-mannose (α-form sugar, $C_6H_{12}O_6$), L-serine (amino acid, $HOCH_2CH(NH_2)COOH$), L-sorbose (open ring sugar, $C_6H_{12}O_6$), DL-tartaric acid (racemic acid, 2-dihydroxy-butanedioic acid), L-tartaric acid (fruit acid, [R-(R*,R*)]-2,3-dihydroxy-butanedioic acid), D-tartaric acid (levorotary/dextro configuration, [S-(R*,R* )]-2,3-dihydroxy-butanedioic acid), L-tryptophan (amino acid, 2-amino-3-propionic acid), and L-tyrosine (amino acid, β-(p-hydroxy-phenyl) alanine.

Table 1, below, shows Mueller matrix detection of isomers of tartaric acid by neural network pattern recognition. Table 1 at column 15 formatted the differential element data $\Delta\underline{M}_{ij}(\lambda_r,\alpha)-\Delta\underline{M}_{ij}(\lambda_0,\alpha)$ for the stereoisomers of tartaric acid to illustrate the neural model's input fields and network training/testing/validation data structure. $\Delta\underline{M}$ are scaled and distributed feature differential elements and DIST is a user-select distribution function bounded by ±1. A binary 1(0) in columns 2–12 implies the active (deactivate) differential element (i,j) measurement, and $1/\lambda_r$ and $1/\lambda_0$ are inverse laser beam wavelengths on and off the absorption band of the analyte, respectively. The correlation coefficient is measured between sets $\{\Delta M(\alpha_i, \lambda_0)\}$ and $\{\Delta M(\alpha_i, \lambda_r\}$ where α ranges from normal incidence 90.00°±20° in 0.01° degree increments and the output vector identifies the analyte as belonging to a unique class.

TABLE 1

| 1 ANALTE | 2 1,2 | 3 1,3 | 4 1,4 | 5 2,1 | 6 2,3 | 7 2,4 | 8 3,1 | 9 3,2 | 10 3,4 | 11 4,2 | 12 4,3 | 13 $1/\lambda_r$ ($cm^{-1}$) | 14 $1/\lambda_0$ ($cm^{-1}$) | 15 Scaled Difference-element Distribution ($\Delta\underline{M}$) | 16 Corr. Coeff | 17 Output Vector |
|---|---|---|---|---|---|---|---|---|---|---|---|---|---|---|---|---|
| DL Tartaric Acid | 0 | 0 | 0 | 0 | 0 | 1 | 0 | 0 | 0 | 0 | 0 | 887.3 | 1038.4 | 0.211*(1 + 0.112*DIST(−1,1)) | −0.075 | (1,0,1,1) Class 12 |
| DL Tartaric Acid | 0 | 0 | 0 | 0 | 0 | 0 | 0 | 0 | 0 | 1 | 0 | 887.3 | 1038.4 | −0.068*(1 + 0.053*DIST(−1,1)) | −0.019 | (1,0,1,1) Class 12 |
| L Tartaric Acid | 0 | 1 | 0 | 0 | 0 | 0 | 0 | 0 | 0 | 0 | 0 | 1082.3 | 1029.9 | 0.105*(1 + 0.029*DIST(−1,1)) | −0.001 | (1,1,0,0) Class 13 |
| L Tartaric Acid | 0 | 0 | 0 | 1 | 0 | 0 | 0 | 0 | 0 | 0 | 0 | 1082.3 | 1029.9 | 1.587*(1 + 0.081*DIST(−1,1)) | −0.089 | (1,1,0,0) Class 13 |
| L Tartaric Acid | 0 | 0 | 0 | 0 | 0 | 0 | 1 | 0 | 0 | 0 | 0 | 1082.3 | 1029.9 | −1.101*(1 + 0.270*DIST(−1,1)) | −0.074 | (1,1,0,0) Class 13 |

TABLE 1-continued

| 1<br>ANALTE | 2<br>1,2 | 3<br>1,3 | 4<br>1,4 | 5<br>2,1 | 6<br>2,3 | 7<br>2,4 | 8<br>3,1 | 9<br>3,2 | 10<br>3,4 | 11<br>4,2 | 12<br>4,3 | 13<br>$1/\lambda_r$<br>($cm^{-1}$) | 14<br>$1/\lambda_0$<br>($cm^{-1}$) | 15<br>Scaled Difference-element Distribution ($\Delta\underline{M}$) | 16<br>Corr. Coeff | 17<br>Output Vector |
|---|---|---|---|---|---|---|---|---|---|---|---|---|---|---|---|---|
| L Tartaric Acid | 0 | 0 | 0 | 0 | 0 | 0 | 0 | 0 | 1 | 0 | 0 | 1082.3 | 1029.9 | 0.099*(1 + 0.015*DIST(−1,1)) | −0.031 | (1,1,0,0) Class 13 |
| L Tartaric Acid | 0 | 0 | 0 | 0 | 1 | 0 | 0 | 0 | 0 | 0 | 1 | 1082.3 | 1029.9 | 0.003*(1 + 0.005*DIST(−1,1)) | −0.060 | (1,1,0,0) Class 13 |
| D Tartaric Acid | 0 | 1 | 0 | 0 | 0 | 0 | 0 | 0 | 0 | 0 | 0 | 1082.3 | 1029.9 | 0.552*(1 + 0.222*DIST(−1,1)) | −0.080 | (1,1,1,0) Class 14 |
| D Tartaric Acid | 0 | 0 | 0 | 0 | 0 | 1 | 0 | 0 | 0 | 0 | 1 | 1082.3 | 1029.9 | 0.011*(1 + 0.032*DIST(−1,1)) | −0.198 | (1,1,1,0) Class 14 |

The experimental values of $\Delta\underline{M}_{ij}$ per $\lambda_r$, $\lambda_0$ beam pair in Table 1 (the feature differential elements) are the most significant network variable. These domains are selected from the complete field of 15 normalized-elements of the Mueller matrix that are statistically disjoint. They are disjoint in the sense that there is no overlap between sets from their average value±one standard deviation, $\Delta\underline{M}_{ij}(\lambda_r,\alpha) \cap \underline{M}_{ij}(\lambda_0,\alpha)=\emptyset$, from a range of beam orientations $\alpha=90.00°\pm20.00°$ in 0.01° increments (i.e., 4000 measured elements per set). $\lambda_r$ and $\lambda_0$ are beam wavelengths corresponding to the analyte's vibration resonance and nonresonance states, respectively, and $\alpha=90.00°$ is normal beam incidence. Each data entry of column 15 in Table 1 is of the form:

$$\Delta\underline{M}_{ij}(\lambda_0,\lambda_r,\alpha=90.00°)[1+SD\cdot DIST];$$

where the underbar symbol implies auto-scaling of the differential Mueller matrix element, SD is standard deviation of the scaled set $\{\Delta\underline{M}_{ij}(\lambda_0,\lambda_r,\alpha)\}$, and DIST is some distribution function bounded by ±1.

Auto-scaling is sometimes referred to as "mean centering and variance normalization". It allows $\{\Delta\underline{M}_{ij}\}$ with different dynamic ranges to be compared directly, thus eliminating a constant offset in DIAMMS measurements by all organic compounds tested over all angles and wavelengths, and is computed as:

$$\Delta\underline{M}_{ij}(\lambda_0,\lambda_r,\alpha)=(\Delta\underline{M}_{ij}(\lambda_0,\lambda_{r,\alpha)-<\{\Delta}\underline{M}_{ij}(\lambda_0,\lambda_r,\alpha)\}>)/4*SD,$$

where the mean value of the matrix measurement is designated by brackets < >. The distribution function DIST of Table 1 gives weight to and spreads the $\Delta\underline{M}_{ij}$ variable over a range of ± one SD of the set average. In these models, a linear DIST function is used in building network training and testing data sets. For example, the variable $\Delta\underline{M}_{2,4}$ in column 15 of row of Table 1 is distributed as 0.211 (1±0.112n) for n=0, 0.1, 0.2, . . . 1.0, and interpolated between values during network training. This group is distributed to node 14 of the network input layer and associates racemic tartaric acid to output vector (1,0,1,1) or CLASS 12 from a total of 16 classes. More accurate predictions may result from clustering the $\Delta\underline{M}_{ij}$ input field via a Gaussian distribution, and/or other suitable DIST functions.

The neural network input data field also includes binary header input variables shown in columns 2–12 of Table 1. A binary 1 in these columns tags the susceptible matrix differential element per beam wavelength pair designate. None of the diagonal matrix elements appear as features in all of the organic compounds tested, as these elements are all positively correlated and overlapping, and not selected. Additionally, the correlation coefficient between $\{\Delta\underline{M}_{ij}(\alpha, \lambda_r)\}$ and $\{\Delta\underline{M}_j(\alpha, \lambda_0)\}$ angular scans in all feature elements is slightly negative, shown in column 16 of Table 1. In Table 1, column 17, each biosimulant is assigned a unique binary 4-vector with class designate. The network weight matrix correlates this vector to chemical identity.

FIG. 1 is a representation of the scaled and distributed difference Mueller matrix elements most susceptive to stereoisomers of tartaric acid in backscattering on and off its molecular vibrational resonance line plotted in Mueller matrix space, showing the three most significant difference elements of levorotary tartaric acid and two difference elements of the dextrorotary form. As seen in FIG. 1, the feature differential elements of isomers of tartaric acid, listed in Table 1, are plotted in Mueller matrix space. The centroids of these entities (Table I, column 15, n=0) have coordinates $(\Delta\underline{M}_{13}, \Delta\underline{M}_{21}, \Delta\underline{M}_{31})=(0.105,1.587,-1.101)$ and $(\Delta\underline{M}_{13}, \Delta\underline{M}_{43})=(0.552,0.011)$ for levorotary and dextrorotary forms of the organic molecule, respectively. Rectangular dimensions of these domains represent twice the standard deviations in sets $\{\Delta\underline{M}_{13}, \Delta\underline{M}_{21}, \Delta\underline{M}_{31}, \Delta\underline{M}_{43}:\alpha=90.00°\pm0.01°n, n=0,1,2, 3, . . . ,2000\}$, known as "detection domains in Mueller matrix space". The basis, or number of axes, cannot exceed 15. L-tartaric acid, which occupies a 5-dimensional Mueller space, is plotted along its three most significant feature differential elements in FIG. 1, for graphical brevity. Detection domains of three forms of tartaric acid and 15 other biosimulants are grouped per analyte and passed to the $14^{th}$ node, or neuron, of the neural network input layer when network training is initiated; along with wavelength, correlation, and header nodal input variables. The network architecture accepting these data comprises an input layer of 15 nodes, shown at columns 2–16 in Table 1, an output layer of 4 nodes, shown at column 17 in Table 1 representing components of a 4-vector, and a single, fully connected, hidden-layer with 200 nodes. A successful mapping of incoming sensor data by the trained network weight matrix onto an analyte's Mueller matrix space, i.e., with $0.98\leqq\sigma\leqq1.00$, triggers a detection alarm event; with $\sigma$ as the normalized inner products of sensor output vector and the training set vectors $(R\cdot T_i)/N$.

Pattern recognition in data produced by a laboratory DIAMMS instrument by two distinct neural network systems, comprising a software and a hardware module, are listed below. These networks produce rapid predictions, from DIAMMS data, of any-of-N contaminants located down-range in the sensor's field-of-view. The software module produced a $C^{++}$ compiled program that is executed in computer RAM. The hardware module is implemented via electronically trainable analog neural network (ETANN) chips housed on a mother circuit board. The hardware-implemented model was trained by a backward-error propagation (BEP) algorithm, a form of the early multi layer perceptron-training rule with gradient descent learning paradigm, in producing the desired network weight matrix, or pattern recognition filter. The software model, which performs all neural computing in random addressable memory of a PC, uses a similar BEP algorithm but with an adaptive gradient learning rule. Additionally, adaptive resonance theory (fuzzy ARTMAP algorithm) was applied to the chemical recognition problem producing neural models with high performance characteristics and accurate prediction capability comparable to BEP. A best-performance BEP model tested from many feed-forwarding trials with experimental DIAMMS data may provide the desirable component to be integrated into a tactical IR polarized light scattering sensor as a pattern recognition module for any-of-N analyte detection.

Software Model

NeuralWorks Predict, a neural network developer's tool from NueralWare, Inc., of Pittsburgh, Pa., was used for building the software model for producing rapid predictions from DIAMMS data. NeuralWorks Predict provides Windows point-and-click access via an Microsoft Excel interface to network training, testing, validation and editing functions; numerous data analyses functions including transformation properties of input and output data fields and network accuracy; and it converts a trained/tested model into C code for embedding into the DIAMMS system. With the computer user interface to Predict in Microsoft Excel 97, the DIAMMS database was transferred into this spreadsheet format via the Windows 95 operating system. The network test and train set included 15 input and 4 output variables comprising columns 2–16 and column 17 of Table 1, respectively. With the $\Delta \underline{M}_{ij}$ data distributed in the linear DIST function, the network training and test set of 16 analytes totaled 1114 rows by 16 columns. In preparation of training the network prediction model all 16 inputs were forced as fit, active variables, with all the variables participating in the model building. Nodes 14 ($\Delta \underline{M}_{ij}$) and 15 (correlation coefficient) were declared as moderately noisy, a comprehensive data transformation option of input and output fields and an exhaustive network search for best accuracy results were selected on software menus. A data transformation property of Predict initially converts the raw input training data, or the spreadsheet of Table 1 format, into a different format that is optimized for network performance, while "exhaustive search" selectively trains several candidate network architectures for "performance scores". Perdict chooses a best performance network from scores on defined fitness functions: such as correlation between training and raw vector outputs closest to 1, or RMS error closest to 0, for example.

While training the network model, Predict incrementally builds hidden layer nodes, starting at a first node, according to prescribed network test functions and fitness and evaluation parameters. As the model proceeds in a training session, performance per epoch is scored via a "common mean correlation" evaluation function with an accuracy tolerance of $2.0 \cdot 10^{-10}$. A myriad of heuristic, learning, neurodynamics and evaluation parameters in Predict were systematically adjusted to produce a common mean correlation score as close to 1 as was possible in training and retraining sessions. The best model that evolved from final training comprises 15 active input layer nodes with 25 transforms 200 hidden layer nodes (neurons), which are the maximum allowable, and 4 output layer nodes producing a mean correlation score of 0.9995. The hidden layer nodes may range from about 150 to about 250. Generally it is believed that the greater number of hidden layer nodes provides a mean correlation score closer to one, however, it is further believed that greater than about 250 nodes does not provide improvement of the mean correlation score. Details of this network's input and output field transforms are listed in Table 2, below.

TABLE 2

| Input/Output | Field | Neuron Transform Functions 3 | | | | | |
|---|---|---|---|---|---|---|---|
| 1 | 2 | Tnn | Tmin | Tmax | Avg | Imin | Imax |
| I | M12 | T01 | logical | 0.00 | 1.00 | 0.000 | 1.000 |
| I | M13 | T01 | logical | 0.00 | 1.00 | 0.000 | 1.000 |
| I | M14 | T01 | logical | 0.00 | 1.00 | 0.000 | 1.000 |
| I | M21 | T01 | logical | 0.00 | 1.00 | 0.000 | 1.000 |
| I | M23 | T01 | logical | 0.00 | 1.00 | 0.000 | 1.000 |
| I | M24 | T01 | logical | 0.00 | 1.00 | 0.000 | 1.000 |
| I | M31 | T01 | logical | 0.00 | 1.00 | 0.000 | 1.000 |
| I | M32 | T01 | logical | 0.00 | 1.00 | 0.000 | 1.000 |
| I | M34 | T01 | logical | 0.00 | 1.00 | 0.000 | 1.000 |
| I | M42 | T01 | logical | 0.00 | 1.00 | 0.000 | 1.000 |
| I | M43 | T01 | logical | 0.00 | 1.00 | 0.000 | 1.000 |
| I | ON-RES | T01 | Linear | −1.00 | 1.00 | Avg 0.830 | 1.095 |
| | | T02 | Log | −1.00 | 1.00 | Avg 0.830 | 1.095 |
| | | T03 | Rt2 | −1.00 | 1.00 | Avg 0.830 | 1.095 |
| I | OFF-RES | T01 | Linear | −1.00 | 1.00 | Avg 0.833 | 1.050 |
| | | T02 | Rt2 | −1.00 | 1.00 | Avg 0.833 | 1.050 |
| | | T03 | ln x/(1 − x) | −1.00 | 1.00 | Avg 0.833 | 1.050 |
| I | SCALED DIFF M | T01 | Linear | −1.00 | 1.00 | Avg −2.279 | 2.959 |
| | | T02 | Inv | −1.00 | 1.00 | Avg −2.123 | 2.959 |
| | | T03 | Pwr2 | −1.00 | 1.00 | Avg −2.123 | 2.959 |
| | | T04 | fzlft | 0.00 | 1.00 | −5.515 | −5.515 −2.123 |
| | | T05 | fzrgt | 0.00 | 1.00 | 2.959 | 6.196 6.196 |
| I | CORR COEFF | T01 | Linear | −1.00 | 1.00 | Avg −0.527 | −0.001 |
| | | T02 | InvPwr4 | −1.00 | 1.00 | Avg −0.527 | −0.001 |
| | | T03 | tanh | −1.00 | 1.00 | Avg −0.527 | −0.001 |
| O | COMPONENT1 | T01 | Linear | 0.00 | 1.00 | Avg 0.000 | 1.000 |
| O | COMPONENT2 | T01 | Linear | 0.00 | 1.00 | Avg 0.000 | 1.000 |

TABLE 2-continued

| Input/ Output | Field | Neuron Transform Functions 3 | | | | | |
|---|---|---|---|---|---|---|---|
| 1 | 2 | Tnn | Tmin | Tmax | Avg | Imin | Imax |
| O | COMPONENT3 | T01 | Linear | 0.00 | 1.00 | Avg 0.000 | 1.000 |
| O | COMPONENT4 | T01 | Linear | 0.00 | 1.00 | Avg 0.000 | 1.000 |

In Table 2, the Neural network transform functions of the trained network are presented, built from a database of 16 biosimulants in the format of Table 1. Input (I), hidden (H) and output (O) neuron layers are grouped in a 15I:200H:4O architecture, discussed below. The network I/O variables are identified in column 2. In column 3, the transform number (Tnn sequence), function, its minimum (Tmin) and maximum (Tmax), the average method of data mapping (Avg), field minimum (Imin), and field maximum (Imax) are listed in order. The last three numerical arguments of the fuzzy logic transforms (fzlft and fzrgt) are left, right, and center transition points.

Results of analyzing the model output node components COM1–COM4 are shown in Table 3. Table 3 shows the Neural network model performance, listed below:

TABLE 3

| Output Field | R | Average Absolute Error | Maximum Absolute Error | RMS Error | Accuracy (20%) | Confidence Interval (95%) |
|---|---|---|---|---|---|---|
| COM1 | 0.9994876 | 0.01024661 | 0.2224883 | 0.0159796 | 0.9991015 | 0.0311022 |
| COM2 | 0.9997403 | 0.00713912 | 0.1222888 | 0.0113437 | 1 | 0.0220790 |
| COM3 | 0.9994625 | 0.01138153 | 0.1632465 | 0.0162508 | 1 | 0.0316301 |
| COM4 | 0.9991296 | 0.1917301 | 0.1917301 | 0.0205607 | 1 | 0.0400188 |

The network training set consists of 16 biosimulants complementing 1113 records (rows in the format of Table 1). COM1–COM4 are the network output fields, R is the linear correlation between actual and predicted outputs of the fully trained network. The errors between predicted and actual outputs are represented in three statistics: average absolute, maximum absolute and root-mean-square error. Accuracy, or fitness of true prediction, is measured to 20% tolerance of the true output. The confidence interval yields deviation of network output from the target value to a 95% confidence level. Column 2 of Table 3 lists linear correlation (R) between the true vector components assigned to each analyte in the training set and the corresponding raw neural network output vector components (the product of feed-forwarding). Columns 3–5 list computations of average absolute error, maximum absolute error, and root-mean squared (RMS) error between these components. Column 6, the accuracy measure, is the fraction of the raw network components within 20% of the true component. The confidence interval of column 7 is a measure of precision of network predictions from these testing trials: the interval is a neighborhood of accuracy to within 95% confidence limits. The confidence interval measurements are valid if the vector component error sets {|prediction—target|$_i$} are normally distributed. Other useful analysis tools such as "error matrix" and "confusion matrix" were scrutinized over greater than 30 trained candidate architectures.

A "FlashCode" option of the Predict program was executed in converting the above neural model into a stream of C code instructions for DIAMMS sensor deployment. The majority of this code comprises weight matrix values. With the above performance characteristics, the pattern recognition module may deliver better than 95% true positive identifications and practically nil false detection field test results when implemented in the DIAMMS prototype detection system.

Hardware Model

Significant advantages in DIAMMS data processing bandwidth and network feed-forwarding processing rates are realized by downloading a trained and tested neural model onto EEPROM hardware. A high-performance pattern recognition system to a tactical thermal luminescence sensor for chemical ground contamination detection using Intel's 80170NX Electrically Trainable Analog Neural Network (ETANN) chip was built and applied. The chip, manufactured by Intel of Santa Clara, Calif., is specified at $\mu$s feed-forward processing speeds or 2 billion nodal interconnects per second. Given the rather complex and lengthy neural architectures needed for accurate chemical pattern recognition, the ETANN was necessary for accomplishing real-time pattern recognition, using the chip's capability of making subsecond detection predictions, close to real-time. The ETANN technology was extended to the DIAMMS detection problem by training a BEP/gradient descent 3-layer network with the database, as described above, except the outputs of column 17 in Table 1 had 0 replaced by −1. The [−1, 1] limits at the network output nodes are also the bounds of the single hyperbolic tangent (tanh) transfer function utilized in this network architecture. A program called DynaMind, a product of NeuroDynamX, Incorporated, of Bolder, Colo., and a product of Intel's Neural Network Training System (INNTS), was used for building a network pattern recognition model and transferring its trained weight matrix quantities to the ETANN integrated circuits.

Figure 2:
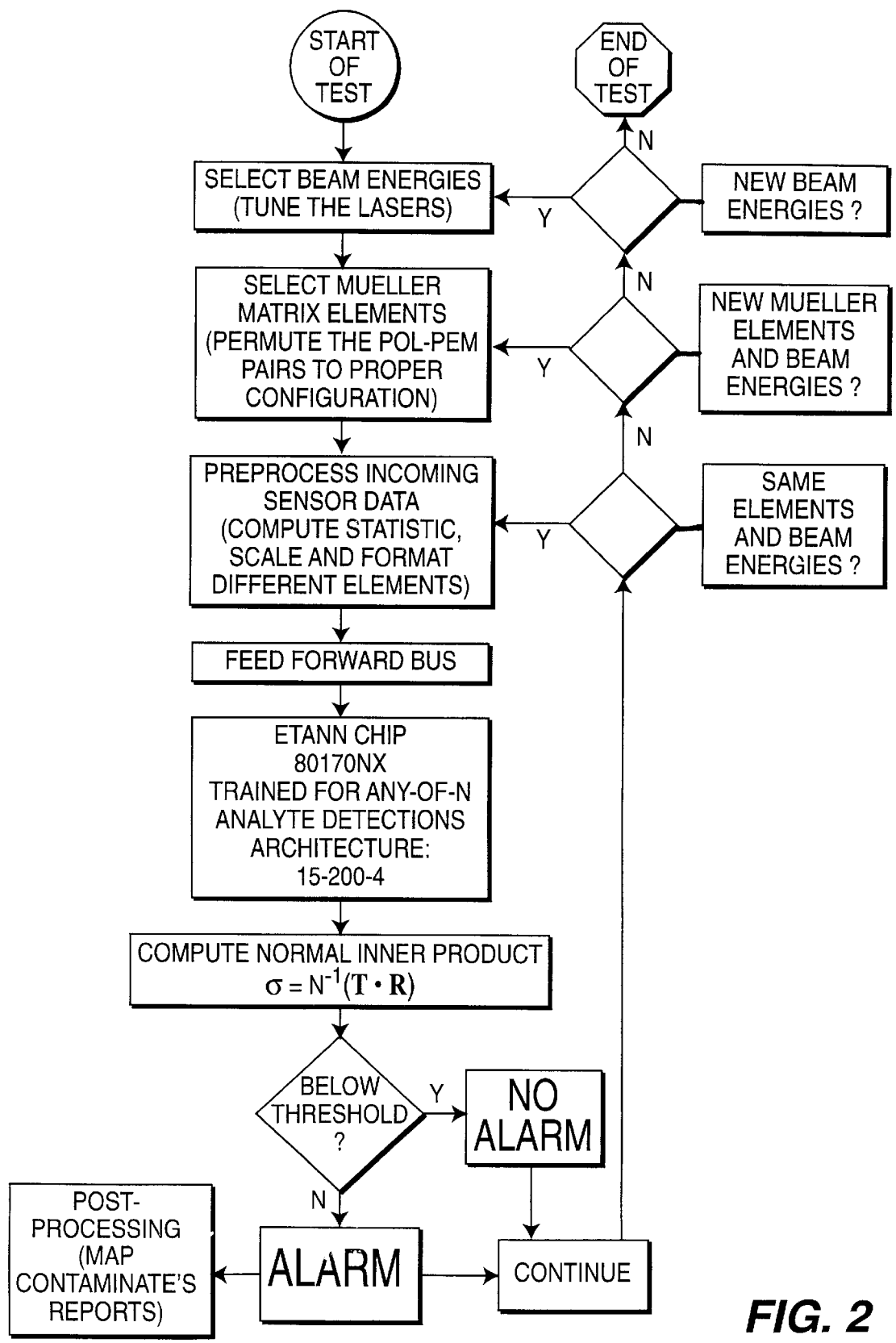

The DIAMMS hardware data acquisition and pattern recognition system is depicted in the flowchart of FIG. 2. Elements of preprocessing the incoming raw sensor data, neural network pattern recognition, decision-making and postprocessing functions are shown as schematic representations of the component parts of the present invention. As seen in FIG. 2, the "Select Beam Energies" and "Select Mueller Matrix Elements" blocks indicate general protocol for operating the sensor. While sequentially emitting it laser beams, the DIAMMS receiver collects modulated backscattered radiance, condenses and then polarization-modulates it a second time. The modulated radiance is focused onto a cooled IR photosensitive surface and recorded as a voltage waveform or scattergram. This scattergram is subsequently preprocessed by phase-sensitive electronics and transformed into the Mueller matrix elements, filtered, formatted as described above, and forwarded to the ETANN for pattern recognition.

DIAMMS preprocessed, filtered and formatted sensor data are conducted via PC bus, linked directly to the ETANN 80170ONX chip, to a downloaded weight matrix through the 15 input nodes (I)—200 hidden nodes (H)—4 output nodes (O) network architecture, referred to as 15-200-4 Input-Hidden-Output layers architecture. The weight matrix transformed these data into real-number components of a 4-vector T presented at the network output layer nodes COM1–COM4, with magnitudes between ±1. Subsequently, a "Compute Normal Inner Product" operation is performed: $\sigma=(T\cdot R)/N$; for each analyte in the network training set, where R is the analyte's basis vector, shown at column 17 in Table 1, and N $(t_1 r_1+t_2 r_2+t_3 r_3+t_4 r_4)^{1/2}$ is the inner product norm. This scalar product, $\sigma$, is the sensor's alarm indicator. Alarming is done from a field 16 biosimulants whose Mueller matrix properties are engrained patterns residing in the weight matrix downloaded in ETANN memory. The range of alarming computed quantities may be determined by those skilled in the art, with a computed quantity of $1 \leqq \sigma \leqq 0.98$ preferably causing the alarm to trip, and activating sensor specific tasks such as GPS mapping of the contaminant mass, radioed reports of relevant properties of the contaminant, threat countermeasure instructions, and/or other applicable information.

The present invention provides the advantageous use of an artificial neural network computing applied to the remote detection problem. As such, it is anticipated that higher prediction accuracy and much lower noise sensitivity occurs when employing properly trained BEP, ARTMAP, or radial-basis function (RBF) networks for chemical and biological detection as opposed to statistical methods such as nearest neighbor classifiers. CBWM signatures for pattern recognition manifest as differences in Mueller matrix elements showing unique susceptibility to the target on-then-off molecular vibration resonance. Even with sensor data containing appreciable noise and cluttered electronic and optical interference, properly trained neural network weight matrices discern the CBWM reliably, generally up to a limit of approximately 30% noise put out by the detection instrument. Beyond this approximately 30% noise level, the trained neural network weight matrices tends to fail catastrophically.

Detecting a plethora of chemical and biological substances in a field environment with a DIAMMS field sensor system from one neural model requires a comprehensive network training/testing/validation set producing an enormous weight matrix. The enormous weight matrix may tax computer processing speed and RAM resources. The hardware network implementation previously discussed can handle pattern recognition of any-of-16 individual compounds with a modern personal computer, such as a Pentium 400 MHz, 528 MB RAM, or better, and interlacing 8 ETANN chips configured for weight matrix sharing. Re-training of the weight matrix may be accomplished on-site to provide additional pattern recognition for a new set of chemical/biological compounds, or adding to the present set of compounds. Moreover, a recently introduced successor Ni1000 neural network chip to the 80170NX may significantly improve processing speeds and increase input variable sizes. With the Ni1000 neural network training system, which uses a RBF training "engine", from Nestor, Inc., of Providence, R.I., increased capabilities in the pattern recognition hardware for the DIAMMS should occur.

EXAMPLES

Several polarization-modulated $CO_2$ laser beams of unequal energy irradiate surfaces suspected of containing chemical and biological warfare agents. The difference elements of the matrix field, on-then-off resonance beam backscattering from the surface, are filtered and applied to a trained and tested neural network pattern recognition system for detection of the known organic compounds. Filtration is done after normalization, scaling, and subtraction operations are performed on the backscattering Mueller matrix elements that are anti-correlated and statistically disjointed under the resonance/non-resonance beam scattering conditions. These Mueller matrix difference elements are unique signatures for the contaminant compounds, per pair of irradiating laser beams.

It should be understood that the foregoing summary, detailed description, and example of the present invention are not intended to be limiting, but are only exemplary of the inventive features which are defined in the claims.

What is claimed is:

1. A neural network pattern recognition system for remotely sensing and identifying chemical and biological materials comprising:

a software component having an adaptive gradient descent training algorithm capable of performing backward-error-propagation and an input layer that is formatted to accept differential absorption Mueller matrix spectroscopic data;

a filtering weight matrix component capable of filtering pattern recognition from Mueller data for specific predetermined materials;

a processing component capable of receiving the pattern recognition from the filtering weight matrix component and determining the presence of specific predetermined materials; and an alarm set within a scalar product value.

2. The system of claim 1, wherein the software component comprises a 15-n-4 Input-Hidden-Output layers architecture, wherein n is from about 150 to about 250.

3. The system of claim 1, wherein the software component is implemented in neural network hardware.

4. The system of claim 1, further comprising a component for implementing post-processing where location and identification is made via a DIAMMS sensor with GPS and radio communication systems.

5. The system of claim 2, further comprising a fully trained weight matrix.

6. A DIAMMS sensor system integrated with the neural network pattern recognition system of claim 1.

7. The system of claim 1, wherein the system is capable of pattern recognition on any-of-N chemical and biological material.

8. The system of claim 1, wherein the system provides real-time detection and identification of said materials.

9. The system of claim 1, wherein the system comprises a global positioning system correlated to the processing component.

10. The system of claim 9, wherein the global positioning system provides an area plot of detection.

11. A method for sensing and identifying chemical and biological materials comprising the steps of:

providing a software component having an adaptive gradient descent training algorithm capable of performing backward-error-propagation and an input layer that is formatted to accept differential absorption Mueller matrix spectroscopic data, a filtering weight matrix component capable of filtering pattern recognition from Mueller data for specific predetermined materials, and, a processing component capable of receiving the pattern recognition from the filtering weight matrix component and determining the presence of specific predetermined materials;

building artificial neural network systems for detecting specific solid organic compounds by pattern recognition of their polarized light scattering signatures;

discerning the presence of specific analytes within a sample based upon cued susceptive Mueller matrix difference elements; and retraining the weight matrix component to add additional chemical/biological compounds.

12. The method of claim 11, further comprising the step of collecting backscattered radiation from the irradiated surface to provide the sample.

* * * * *